United States Patent [19]

Beck et al.

[11] 4,364,797

[45] Dec. 21, 1982

[54] AUTOMATICALLY FED DISTILLATION AND FRACTIONATION SYSTEM

[75] Inventors: Boyd R. Beck, Spring City; Lamar H. Stewart, Gunnison; Steven Tapp, Ephraim; Don L. Anderson, Jr., Gunnison; Daniel E. Nuffer, Ephraim, all of Utah

[73] Assignee: Stil Sun Oil, Inc., Centerfield, Utah

[21] Appl. No.: 287,239

[22] Filed: Jul. 27, 1981

Related U.S. Application Data

[60] Division of Ser. No. 134,878, Mar. 28, 1980, Pat. No. 4,314,890, which is a continuation-in-part of Ser. No. 83,281, Oct. 10, 1979, abandoned.

[51] Int. Cl.$^3$ .......................... B01D 3/02; B01D 3/42
[52] U.S. Cl. .................................... 202/181; 202/193; 202/196; 202/206; 202/234
[58] Field of Search .................. 203/1, 19, 2, DIG. 1, 203/DIG. 13, DIG. 18; 202/181, 206, 233–235, 193, 196

[56] References Cited

U.S. PATENT DOCUMENTS

| | | | |
|---|---|---|---|
| 102,633 | 5/1870 | Wheeler et al. | 202/234 |
| 3,325,376 | 6/1967 | Eckert | 202/234 |
| 3,330,740 | 7/1967 | Duffy | 202/181 |
| 3,364,731 | 1/1968 | Hook | 202/206 |

*Primary Examiner*—Frank Sever
*Attorney, Agent, or Firm*—Thorpe, North & Western

[57] ABSTRACT

An electrically and/or solar heated distillation and fractionation system for separating ethanol-water mixtures comprised with an insulated inclined vaporization chamber divided into an upper solar absorbent vaporization section and a lower pre-heating section by a vaporization floor, float means to automatically control the ethanol-water feed to the lower portion of the preheating section when distillation is taking place, means to evenly distribute the ethanol-water mixture on the vaporization floor, means to heat the ethanol-water mixture in the distillation chamber, a packed fractionation column through which the vapors from the distillation chamber must pass, means to control the temperature at the top of the fractionation column-condensing means to recover and/or recycle distillate exiting to the upper portion of the distillation column and means to remove or recycle residual aqueous liquid from the lower end of the vaporization section.

5 Claims, 5 Drawing Figures

AUTOMATICALLY FED DISTILLATION AND FRACTIONATION SYSTEM

BACKGROUND OF THE INVENTION

This application is a division, of application serial no. 134,878, filed 3/28/80, now U.S. Pat. No. 4,314,890, which is a continuation in part of our earlier application, Serial No. 083,281, filed October 10, 1979, now abandoned.

This invention relates to a system and method for the solar and/or electrical distillation of ethanol from ethanol-water mixtures. More particularly, this invention relates to a system and method for the separation of ethanol from ethanol-water mixtures wherein the feed to the distillation device is automatically controlled so as to feed water-ethanol mixtures to the distillation chamber only when the chamber is sufficiently hot to allow distillation to take place.

The distillation of ethanol from ethanol-water mixtures is well known for the recovery of ethanol for alcoholic beverages and for industrial purposes. However, with the recently spiraling costs of fossil-based fuels, the utilization of ethanol in internal combustion engines has become increasingly important. Ethanol may be prepared naturally by fermentation and may also be prepared by industrial processes such as the hydration of ethylene. In both methods of manufacture, a dilute aqueous solution of ethanol is formed requiring the ethanol to be removed from the greater portion of the water in order for it to function effectively as a fuel in an internal-combustion engine. In Ser. No. 083,281 an apparatus and method for removing ethanol from ethanol-water mixtures was disclosed wherein the ethanol-water mixtures were preheated by solar means in a separate preheating zone and was then passed to a solar vaporization chamber wherein the ethanol was distilled or vaporized from the water utilizing solar energy as the primary or sole source of heat.

While the above-mentioned invention provides an extremely improved method for the utilization of solar energy, there are many times when such energy is not readily available. Moreover, there are times when the combined utilization of solar and other forms of energy might operate more economically when other factors are taken into consideration.

OBJECTS AND SUMMARY OF THE INVENTION

It is therefore an object of the present invention to provide an efficient system for the separation of water-ethanol mixtures by either solar or electrical energy or a combination of both.

It is also an object of the present invention to provide a system for the separation of water-ethanol mixtures wherein the feed to the vaporization apparatus is controlled by the temperature of the water-ethanol mixture and rate of distillation within the vaporization chamber.

It is further an object of the present invention to provide a system for the separation of water-ethanol mixtures wherein the mixture to be separated is preheated in a chamber immediately adjacent to the vaporization chamber wherein the same energy is used to both preheat and vaporize the mixture and is also used to control the rate at which water-ethanol mixture is fed through the preheating chamber.

These and other objects are accomplished by means of an inclined still, heated by solar electrical or a combination of solar and electrical energy, combined with a fractional distillation column wherein vapors from the chamber are removed through the column. The temperature at the top of the column is preferably maintained at a relatively constant temperature indicative of the purity of the ethanol to be recovered. The inclined still comprises a lower preheating section and an upper vaporization floor. Water-ethanol mixtures entering the preheating chamber are heated by means of solar energy striking the vaporization floor or by means of electrical resistance heaters contained within the preheating chamber and adjacent the vaporization floor. As the water-ethanol mixture is heated, the specific gravity of the mixture becomes less dense allowing the mixture to expand and eventually boil causing the mixture to rise to the top of the preheating section and spill over onto the vaporization floor whereby the ethanol is separated from the aqueous solution and is passed into the fractionation column. Only vapors rich in ethanol reach the top of the column and are recovered as fuel grade ethanol or are recycled back to the preheating section if the ethanol content of the recovered mixture is not sufficiently high. The residual liquid at the bottom of the vaporization chamber is removed and disposed of or recycled back to the preheating section depending upon the ethanol content of such residual liquid. The feed of water-ethanol to the still is controlled by the temperature of the water-ethanol mixture in the apparatus and the rate of ethanol distillation. The water-ethanol feed is controlled by a float valve such that when the still is not working the liquid level within the feed container housing the float valve and the liquid level within the still are the same. As the still is heated and the water-ethanol mixture within the preheating action expands and begins to vaporize or be distilled, the level of the water-ethanol mixture in the feed chamber is lowered and the float valve opens permitting additional feed to enter into the feed chamber. However, the feed entering into the feed chamber through the float valve is controlled by the rate at which the ethanol is removed from the ethanol-water mixture within the still.

The purity of ethanol recovered from the distillation chamber is preferably attained by controlling the temperature at the top of the fractional distillation column. However, an hydrometric valve such as disclosed in Ser. No. 083281 may also be used.

DRAWINGS OF THE INVENTION

DETAILED DESCRIPTION OF THE INVENTION

Figure 1:
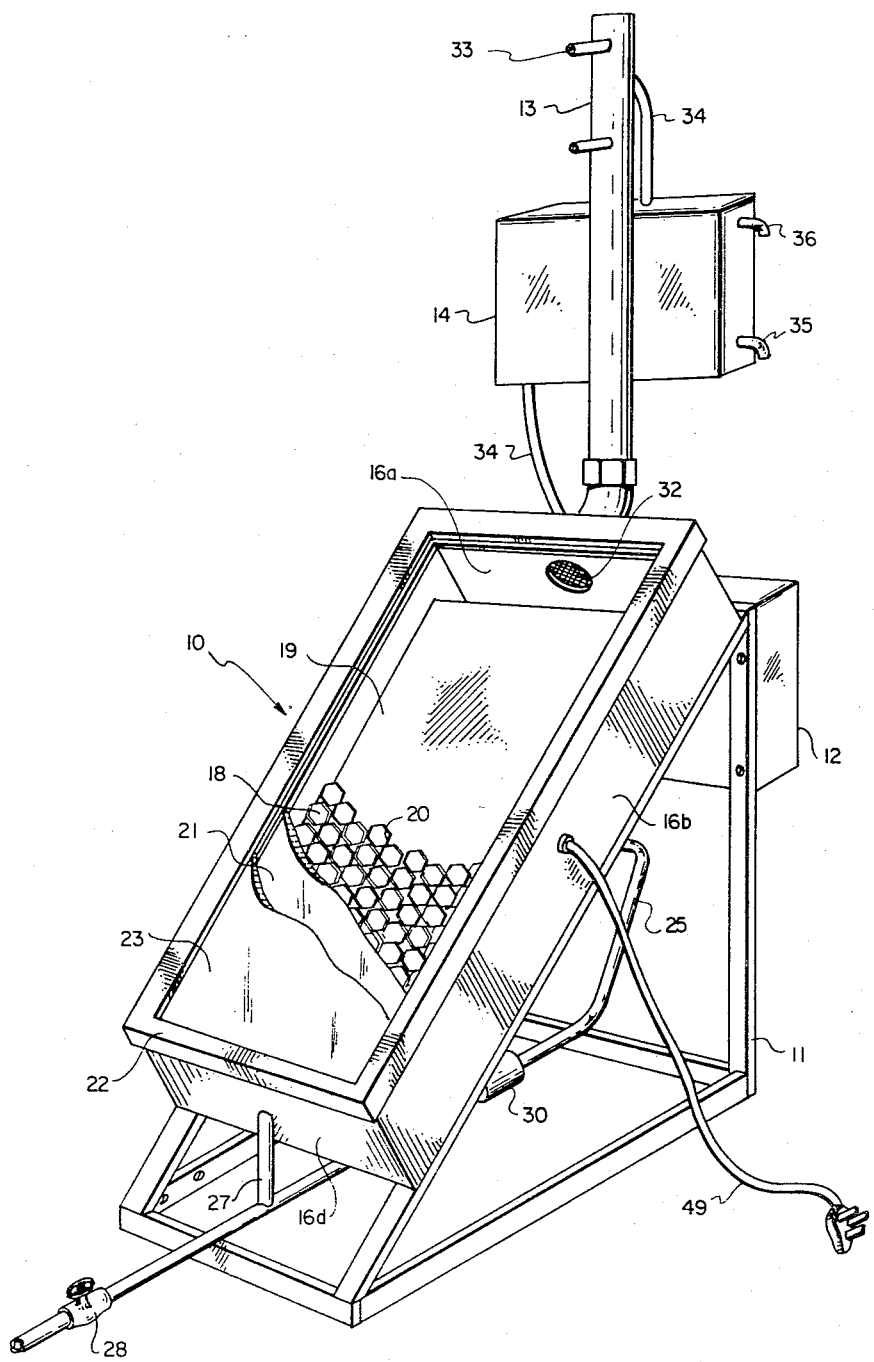
FIG. 1 is a front perspective view of the preferred embodiment of the invention partially broken away in order to illustrate the vaporization section of the apparatus.
Figure 2:
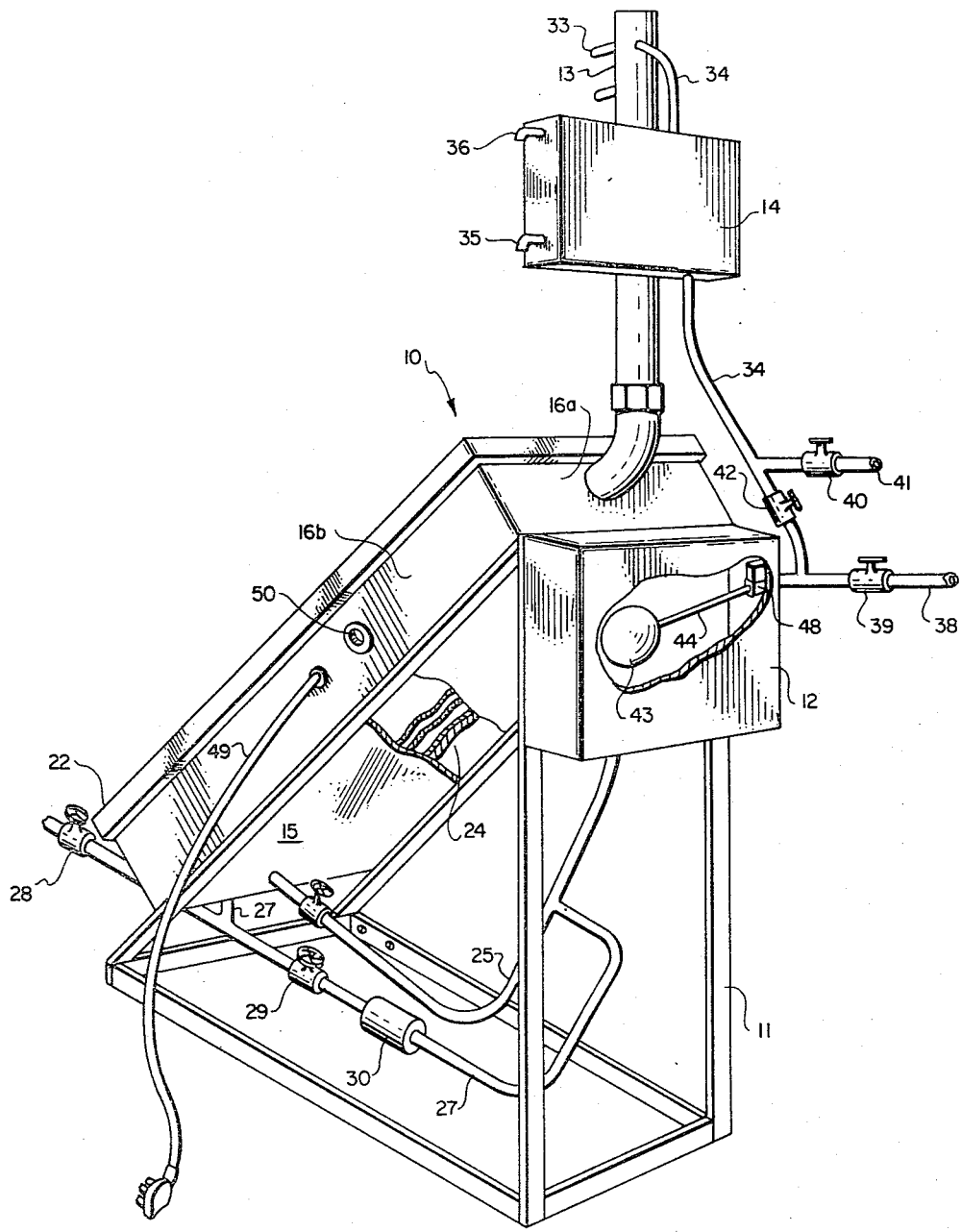
FIG. 2 is a rear elevational view of the apparatus shown in FIG. 1 partially broken away to show the preheating section of the apparatus and the float valve of the feed chamber.
Figure 3:
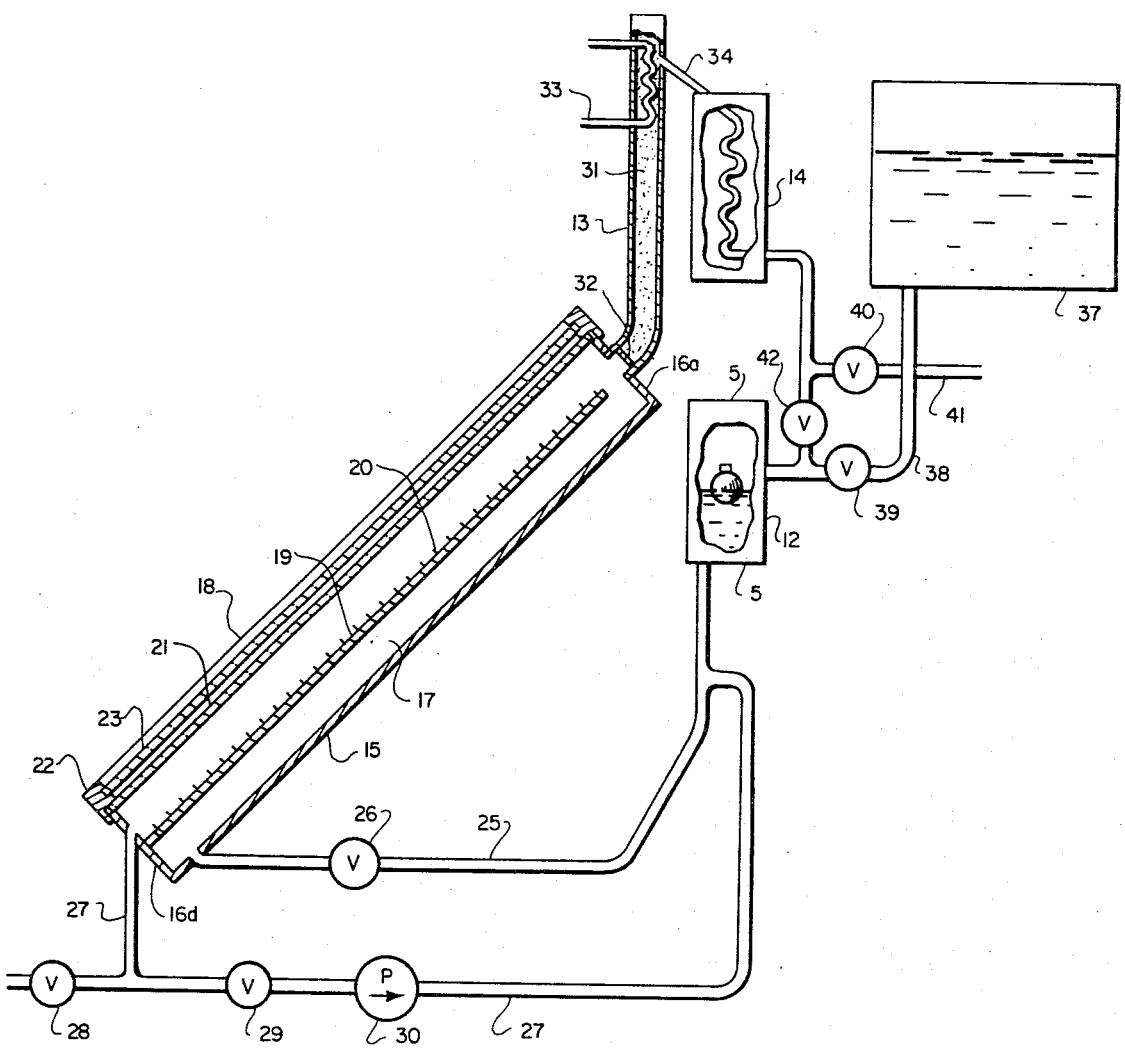
FIG. 3 is a side cross-sectional view of the apparatus shown in FIG. 1 taken along line 3—3 thereof and also contains a schematic flow diagram showing the operation of the apparatus.
Figure 4:
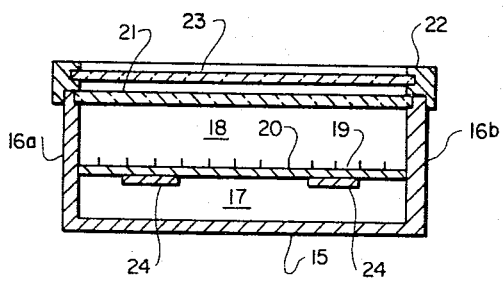
FIG. 4 is a transverse cross-sectional view of the apparatus shown in FIG. 1 taken along line 4—4 thereof.
Figure 5:
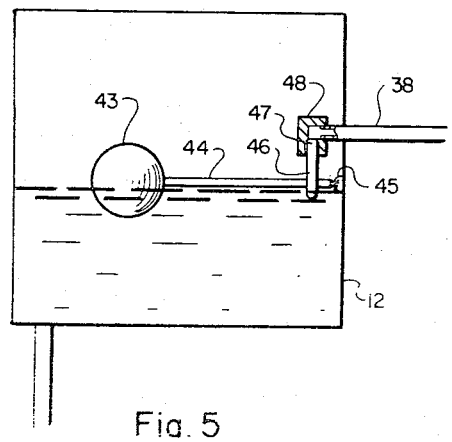
FIG. 5 is a cross-sectional view of the feed chamber showing one type of level control float and valve arrangement taken along lines 5—5 of FIG. 3.

There is shown in FIGS. 1 through 5 a complete and preferred embodiment of the invention. While water-ethanol mixtures from various sources may be utilized in this invention, the apparatus will be described in terms of the separation of the water-ethanol mixture containing about 9 to 13% ethanol. This is representative of water-ethanol mixtures obtained by the natural fermentation of carbohydrate sources.

The apparatus as shown consists of an inclined still 10 supported by a stand 11. A feed chamber 12 is connected to the rear of the still 10. A fractionation column 13 and condenser 14 is connected to and located above the apparatus.

The still 10 is generally rectangular in shape having a generally flat insulated floor 15 surrounded on each side by insulated upwardly extending walls 16a, b, c and d. Dividing the still into a preheating chamber 17 and a vaporization chamber 18 is a vaporization floor 19. Preferably floor 19 is a metal having a solar absorbent surface and contains small solar absorbing projections 20 which inhibit the downward flow of water-ethanol solution thereby allowing sufficient time for ethanol distillation from such solutions. Projections 20 may consist of expanded metal sheets having a honeycomb of similar configuration placed over the vaporization floor 19. Such expanded metal sheets are commonly used in the construction industry as a base for plaster. This type of floor is a considerable improvement over the fabric type of material disclosed in Ser. No. 083,281 in that the floor does not become plugged by foreign matter but remains free of foreign matter since liquid flowing over the expanded metal surface washes these materials from this surface. Floor 19 is contiguous with lower end wall 16d and sidewalls 16b and 16c but terminates short of upper end wall 16a to enable the water-ethanol from the preheating chamber 17 to spill over the upper end of vaporization floor 19 onto the upper projections 20. It follows that the upper end of floor 19 must be horizontally level so that the water-ethanol mixture will be uniformly distributed onto the surface of floor 19. The actual distance between the upper end of floor 19 and end wall 16a is not critical as long as there is sufficient room for removal of distilled vapors from both chambers 17 and 18 of the still 10 into fractionation column 13.

The still 10 contains one or more transparent or translucent covers which are capable of transmitting solar energy. Depending upon the climatic conditions, two or more layers may be used. The primary cover 21 is preferably sealed into walls 16 by appropriate means such as gaskets, caulking and the like. A lid 22 containing one or more layers of glass or plastic 23 may be placed about the upper edges of walls 16 and over cover 21. Each layer of covering, i.e., layers 21 and 23 is separated from each other by a dead-air space. When constructed in this manner the transmission of light through the cover is not inhibited but the outward loss of heat within the vaporization chamber is effectively prevented. Moreover, cover 21 remains heated thereby helping prevent the collection of condensed vapors thereon as is done in conventional solar stills.

Floor 15, the lower end wall 16d and sidewalls 16b and 16c are insulated to retain heat. Any form of insulation conventionally used which will provide an R-15 to R-30 rating is adequate. Typical of such insulating materials are urethane and polystyrene foams. The upper wall 16a is also preferably insulated but need not be.

Attached to the underside of vaporization floor 19 and running essentially the length thereof are one or more electrical resistance heaters 24 which are positioned so as to heat liquid contained in preheating chamber 18 and also heat the surface of vaporization floor 19.

A line 25 closeable by valve 26 interconnects feed chamber 12 with the lower portion of preheating chamber 17. A drain or recycle line 27 whose flow direction is controlled by drain valve 28 or recycle valve 29 and pump 30 completes the plumbing of the still 10 except for fractionation, column 13.

The fractionation column 13 is interconnected with still 10 via an aperture in upper end wall 16a; Column 13 is packed with glass beads, glass wool or any other conventional packing material 31 commonly used in fractionation columns. A retaining screen 32 or glass wool plug prevents the packing material from entering the still 10 while allowing vapors from the still to enter the column. The walls of column 13 are insulated in essentially the same manner as the walls of the still. Preferably, a coiled water line 33 is placed in the upper end of fractionation column 13 adjacent outlet line 34. Liner 34 passes through condenser 14 which is essentially a water-cooled jacket having an inlet 35 and outlet 36.

The water-ethanol feed system may have an optional water-ethanol storage tank 37 connected to feed chamber 12 via line 38 which may be closed by valve 39. Line 34 from the fractionation column and passing through condenser 14 either interconnects line 38 when valve 40 is closed or ethanol product withdrawal line 41 when valve 42 is closed and valve 40 is open.

The flow of water-ethanol through the still is controlled by means of a float control valve located in feed chamber 12. Various valves can be used and thus the invention is not to be limited to the specific embodiment disclosed herein. Basically, the valve control consists of a float 43 attached to an arm 44 which is connected to a wall of feed chamber 12 via a swivel 45. A valve stem 46 interconnects the arm 44 a short distance away from swivel 45. A hydraulic valve head 47 adapted to seat in fluid tight relationship into valve chamber 48 completes the feed system. The feed chamber 12 is positioned relative to still 10 such that the level of liquid in the preheating chamber 17 of the still will be just below the upper end of vaporization floor 19 when the level of liquid in the feed chamber raises the float 43 high enough to seat valve head 47 into the valve body 48 thereby closing off line 38.

With the system described above, the specific mode of operation will now be disclosed.

A water-ethanol mixture prepared by fermentation or synthetically is stored in tank 37. When valves 39 and 26 are opened, feed chamber 12 and preheating chamber 17 are filled by means of fluid flow via lines 39 and 25. As the water-ethanol mixture approaches the top of vaporization floor 19 in chamber 17 feed chamber 12 also fills causing float 43 to rise thereby thrusting valve head 47 into the valve body 48 and shutting off the fluid flow by hydraulic pressure.

As previously taught, still 10 may be heated by solar heat, electrically supplied heat or a combination of both. The positioning of the still relative to the sun as taught in Ser. No. 083,281 may be applied to the present invention. Electrical energy, when used, is supplied to resistance heaters 24 via electrical line 49. A thermostat 50 may be used to control the flow of current to the heaters to provide the desired temperature within the still and allow for optimum usage of solar energy. As the temperature within the still rises, the water-ethanol mixture in preheating chamber expands and eventually boils causing the solution to overflow onto the upper surface of vaporization floor 19. The expanded metal barriers 20 delay the downward flow of the water-ethanol mixture.

The distillation process begins in the preheating chamber 17 and is intensified in vaporization chamber 18. The liquid passing downward along floor 19 becomes progressively more ethanol depleted as it approaches the lower end of chamber 18. Therefore, the liquid reaching the end of chamber 18 consists primarily of water with only minor amounts of ethanol. This ethanol depleted water is withdrawn via line 27 through valve 28 and is discarded. However, if the ethanol content is sufficiently high, valve 28 may be closed and valve 29 opened allowing the liquid to be recycled by pump 30 back to line 25. If desired, a hydrometric valve as disclosed in Ser. No. 083,281 may be used to determine ethanol content and effect recycle. On the other hand, periodic analysis may be made of this residual solution by a hydrometer or a gas chrometograph or other conventional means in order to determine whether to recycle or discard the residual solution.

As the solution within chamber 17 spills over onto the floor of chamber 18, the water-ethanol within feed chamber 12 feeds by gravity flow into chamber 17. This causes the float 43 to lower thereby unseating valve head 47 and allowing fresh feed from tank 37 to enter the feed chamber. As long as the temperature in still 10 remains sufficient to sustain distillation, the feed will be continuous. However, once the temperature in the still drops, the float automatically rises causing the valve head to seal off the flow of feed to feed chamber 12. Thus, water-ethanol mixture cannot flow through the still in the absence of adequate distillation temperatures. Moreover, the still operates automatically thereby lessening the need of having an operator constantly monitoring the still.

As the temperatures within the vaporization chamber 18 become operational, the insulated cover 21 becomes sufficiently warm that ethanol vapors do not condense on the underside thereof. Therefore, essentially all of the vapors within both chambers of the still rise upwardly and enter fractionation column 13. These vapors, depending upon the temperature within the still, consist primarily of ethanol with varying amounts of water.

The Column 13 functions to separate the lower boiling ethanol from the higher boiling water through a series of redistillations as commonly occurs in any fractionation column with the higher purity ethanol vapors passing to the upper portion of column 13 and through line 34 into condenser 14. Surprisingly, it has been found that the vapors entering the column can be fractionated to produce a high quality ethanol with a column which is shorter and less densely packed than is required with a conventional reflux fractional distillation system. A coiled water line 33 is preferably placed in the top of the fractionation column 13 to regulate the purity or concentration of ethanol vapors existing line 34 and being condensed in condenser 14. The temperature of water flowing through line 33 is carefully regulated by means, not shown, to liquify vapors having two high a water concentration and prevent them from passing out of the column via line 34. In this manner the concentration of ethanol leaving the fractionation column can be controlled. For example, at 78.1° C. vapors exiting column 13 would contain 92% w ethanol whereas the condensed liquid would have 91% w or less ethanol. At 81.2° C. vapors exiting column 13 would contain 80% w ethanol whereas the condensed liquid would contain equal weights of water and ethanol. Through published tables, such as is contained on page 2117 of the Handbook of Chemistry and Physics, 39th Edition published by the Chemical Rubber Publishing Company, the optimum temperatures in coiled line 33 for a given ethanol concentration may be determined. The vapors condensed in column 13 are either redistilled in the column or pass downwardly into the still for redistillation.

The vapors passing through condenser 14 are liquified by heat exchange with cold water passing through the condenser via lines 35 and 36 and pass through valve 40 into line 41 for collection as fuel grade ethanol. If the temperature at the top of the fractionation column is not carefully controlled or if, for any other reason, the concentration of water in the ethanol is too high, valve 40 may be closed and valve 42 opened in order to recycle the condensate back to feed chamber 12. In the alternative, this product could be recycled directly to line 25 and by-pass the feed chamber 12. If desired valves 40 and 42 could be replaced by a single hydrometric valve as disclosed in Ser. No. 083,281.

When operating the invention as described above, the temperatures within the still may vary somewhat. Preferably the temperatures will be between about 80° and 95° C. in order to produce a fuel grade ethanol which is 160 proof or better. However, lower temperatures may be used for ethanol of lesser concentrations. It is also possible to utilize the system described herein to separate other liquids having different boiling points such as solvent-resin mixtures.

The following examples were carried out utilizing the system described above and are illustrative of the invention but are not to be considered as limitations thereof. For example, in certain examples a lower quality ethanol is produced due to the lack of temperature control in the fractionation column. Thus, a two-stage distillation is required to provide a higher grade of ethanol. It is apparent from the following examples that the invention may be utilized to produce various grades of ethanol and that a plurality of stills arranged in parallel or in series may be interconnected to obtain the grade of ethanol desired.

EXAMPLE I

The apparatus set up for this example included an inclined still 18×46 inches in size having a 3.5 gallon preheating chamber capacity. A tank containing an auto-automatic float control valve was fed by gravity from a 50 gallon barrel, and the still was fed from the tank. A fractionation column 3 inches in diameter and 48 inches long was utilized which did not contain the temperature control coil at the top.

A 17.5 gallon sample of 24 proof alcohol from a mash fermentation process was placed in the barrel and fed to the tank and still. As the preventing chamber of the still filled to near capacity, the float control valve in the tank closed preventing the dilute alcohol from overflowing into the vaporization chamber of the still. The still and contents were at an ambient temperature of about 18.5°

C. This example was conducted indoors without the use of solar energy.

The still was plugged into a 220 volt electrical outlet and a meter reading was taken. After 22 minutes, the temperature within the still had risen to 88.3° C., and the water-ethanol solution in the preheating chamber began to boil. Six minutes later, the first drop of distilled ethanol was collected resulting in a start-up time of 28 minutes requiring an electrical consumption of 1.4 kilowatts. After start up, the distillation continued to produce one gallon of approximately 110 proof ethanol every 113.5 minutes requiring an energy consumption of 5.68 kilowatts per gallon. The waste water drained from the bottom of the vaporization chamber was analyzed periodically and averaged approximately 2% volume ethanol.

EXAMPLE II

The procedure followed in Example I was utilized except that the water-ethanol mixture was 10% ethanol, and the still operated to produce one gallon of 105 proof ethanol every 90 minutes with an energy consumption of 4.5 Kilowatts per gallon. The waste water had an average ethanol content of 2.3% by volume.

EXAMPLE III

The 105 proof ethanol obtained from Example II was passed through the still a second time in order to provide a higher purity product. Following is a summation of the results obtained.

| | |
|---|---|
| Start up time | 27 minutes |
| Energy consumed in start up | 1.35 kw |
| Gallons per hour of ethanol production | 1.25 gal/hr |
| Total volume of ethanol produced | 15,900 ml or 4.2 gal. |
| Average proof of ethanol produced | 150–155 proof |
| Total volume of waste water | 9,300 ml or 2.46 gal. |
| Average proof of waste water | 40 proof - 20% v ethanol |
| Kilowatt consumption per gallon of ethanol produced after start up | 2.66 kw/gal to 2.22 kw/gal. |

EXAMPLE IV

A larger inclined still having a vaporization floor surface area of approximately two square meters was used in this example. The still was operated solely by electrical energy. The still was warm from a previous test and, therefore, required only an eight-minute warm up before condensate started collecting from the fractionation column. The still operated at an eight-minute warm up before condensate started collecting from the fractionation column. The still operated at an internal temperature of 94° C. The aqueous feed was controlled by a float valve and had an ethanol content of about 10% v. After start up, the still operated to produce about one gallon of 110 proof ethanol every 45.4 minutes utilizing 4.54 kilowatts of electricity per gallon. At the end of the run, the electricity was turned off and the float valve closed shutting off the flow of feed to the still.

EXAMPLE V

The still utilized in Example IV was again used only this time the feed ethanol was 103 proof. Again, the still was warm; and after a 12-minute start up, the first condensate was collected and the float valve opened allowing the feed solution to enter the still. The float valve was observed to close and open periodically in response to the demand for feed to the still. After start up, the still operated at 88° C. to produce one gallon of 163 proof ethanol every 22.7 minutes. The waste water from the bottom of the vaporization chamber contained 32.5% v ethanol and was saved for recycle.

EXAMPLE VI

The still utilized in Example I is used in this example by modifying the upper portion of the fractionation column to include a constant temperture coil maintained by the circulation of water at a constant temperature of about 80.5° C.

The still is operated at 89.5° C. and is fed with 12% v dilute ethanol. After an initial start up of about 29 minutes, the still is automatically fed by use of a float control valve and produces about one gallon of 164 proof ethanol every three hours of operation leaving a waste product containing about 3% v ethanol. The average energy consumption is about 9 kilowatts per gallon.

We claim:

1. A distillation system for the separation of liquid mixtures which comprises:

an inclined still consisting of sidewalls, a lower endwall, an upper endwall, a bottom floor, and a translucent light transmitting top all being joined together to form a sealed still compartment, said compartment being divided into an upper vaporization chamber and a lower preheating chamber by a vaporization floor sealed to said sidewalls and lower endwall parallel to said bottom floor and translucent top, said vaporization floor terminating at its upper end short of said upper endwall, thereby forming a baffle over which liquid from said preheating chamber may overflow into said vaporization chamber, means located on the top surface of said vaporization floor to impede the downward flow of liquid on said surface, means located in said preheating chamber for heating said vaporization floor and liquid contained in the preheating chamber to a specified temperature, inlet means for introducing liquid mixture feed into the lower end of said preheating chamber, outlet means for removing residual liquid from the lower end of said vaporization chamber, and outlet means in said upper endwall for removing vapors formed within the still compartment;

feed control means interconnected with the inlet means to said preheating chamber for controlling the amount of liquid that flows thereinto, said feed control means consisting of a feed chamber having an inlet and an outlet and a hydraulically operated float control valve, which valve controls the flow of feed liquid through the feed chamber to the preheating chamber, said float control valve being selectively positioned substantially level with said baffle, such that, when liquid in the preheating chamber is below a specified temperature, the valve will remain closed, and when liquid in the preheating chamber is raised to at least said specified temperature, the liquid in the preheating chamber expands in volume, thereby becoming less dense, and is pushed over the baffle end of the vaporization floor by the more dense, cooler liquid feed in the feed chamber that flows by gravity through the outlet of the feed chamber to the preheating chamber, the exiting of liquid feed from the feed chamber causing the float control valve to open, thereby allowing feed liquid to flow through the inlet to the feed chamber as long as the temperature of the feed liquid in the preheating chamber is above the specified temperature and the feed liquid is overflowing the baffle end of the vaporization floor; and an insulated condensation section interconnected with said still compartment consisting of a fractionation column which receives distilled vapors from the outlet means in the upper endwall of the still compartment, and condenser means for receiving and condensing vapors from the fractionation column into a distillate.

2. A distillation system according to claim 1 wherein vaporizatin floor and means to impede the flow of liquids on the vaporizaton floor have solar absorbent surfaces, 3. A distillation system according to claim 2 additionally containing
  (a) means interconnecting said outlet means at the lower end of said vaporization chamber with the inlet means to said preheating chamber adapted to either recycle residual liquid from the vaporization chamber back to said preheating chamber or remove said residual liquid from the system and
  (a) means interconnecting said condenser means with the inlet means to said preheating chamber adapted to either recycle distilled liquid from the condenser mean back to said preheating chamber or remove said distilled liquid from the system, 4. A distillation system according to claim 3 wherein the fractionation column contains means in the upper portion thereof to maintain that portion of the column at a constant temperature.

5. A distillation system according to claim 4 wherein said means consists of a coil through which water is circulated at a constant temperature.

* * * * *